US011021675B2

(12) United States Patent
Chordia et al.

(10) Patent No.: US 11,021,675 B2
(45) Date of Patent: Jun. 1, 2021

(54) PROCESS FOR PRODUCING REFINED OILS FROM BOTANICAL PLANT MATTER USING A SUPERCRITICAL FLUID

(71) Applicants: Lalit Chordia, Pittsburgh, PA (US); Sasikumar Ramesh, Pittsburgh, PA (US)

(72) Inventors: Lalit Chordia, Pittsburgh, PA (US); Sasikumar Ramesh, Pittsburgh, PA (US)

(73) Assignee: Thar Process, Inc., Pittsburgh, PA (US)

(*) Notice: Subject to any disclaimer, the term of this patent is extended or adjusted under 35 U.S.C. 154(b) by 35 days.

(21) Appl. No.: 16/570,275

(22) Filed: Sep. 13, 2019

(65) Prior Publication Data
US 2021/0079315 A1 Mar. 18, 2021

(51) Int. Cl.
C11B 3/00 (2006.01)
A61K 36/185 (2006.01)
C11B 1/10 (2006.01)
A61K 31/047 (2006.01)
B01D 11/02 (2006.01)

(52) U.S. Cl.
CPC ............ C11B 3/006 (2013.01); A61K 31/047 (2013.01); A61K 36/185 (2013.01); B01D 11/0203 (2013.01); C11B 1/104 (2013.01)

(58) Field of Classification Search
CPC ... C07D 311/80; B01D 11/02; B01D 11/0203; C11B 3/006; C11B 1/104
See application file for complete search history.

(56) References Cited

U.S. PATENT DOCUMENTS

| 5,252,729 | A | 10/1993 | De Crosta et al. |
| 8,895,078 | B2 * | 11/2014 | Mueller ................. A61K 31/35 424/725 |
| 9,186,386 | B2 | 11/2015 | Speier |
| 9,333,229 | B2 | 5/2016 | Bjorcrantz |
| 2000/9001111 | | 1/2009 | Marentis |
| 2017/0291120 | A1 * | 10/2017 | Jackson ............ B01D 11/0288 |
| 2018/0344661 | A1 * | 12/2018 | Finley .................. A61K 36/185 |

FOREIGN PATENT DOCUMENTS

WO WO 2018167038 * 9/2018 ............ B01D 11/02

* cited by examiner

Primary Examiner — Yate' K Cutliff
(74) Attorney, Agent, or Firm — Dentons Cohen & Grigsby P.C.

(57) ABSTRACT

An improved process for producing refined oils free of contaminating waxes, resins, and lipids from botanical plant matter using an improved in-line winterization process is disclosed. The biomass is fed into an extraction vessel where the oils are extracted using a solvent, followed by a two-stage separation. Both the temperature and pressure of the solvent going into the separators are controlled for effective separation. Additional solvent is added to enhance the separation efficiency between the refined oil and the undesired fraction containing the contaminants. This process provides an alternative to current wax mitigation techniques, such as alcohol based solvent winterization.

18 Claims, 1 Drawing Sheet

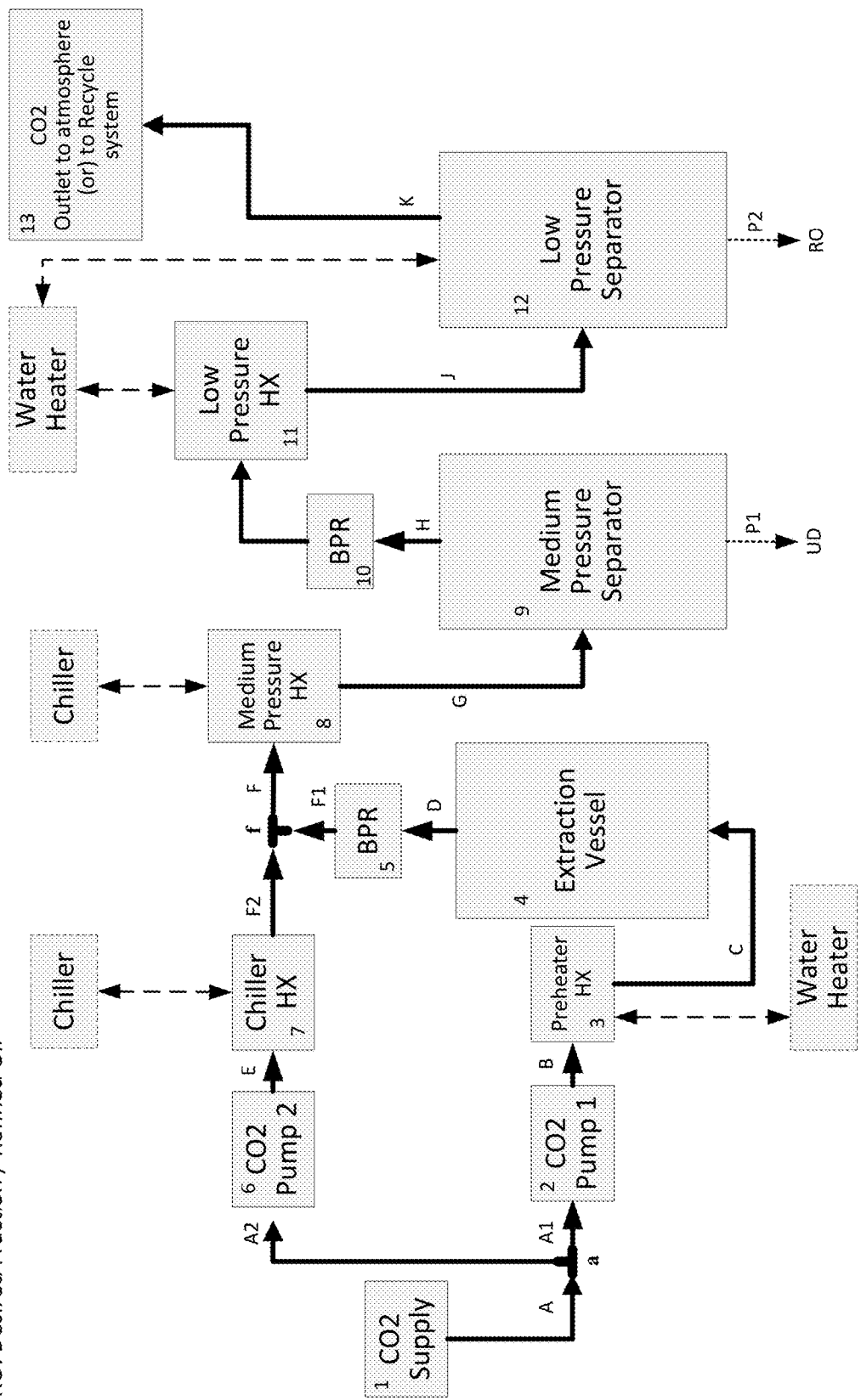

PROCESS FOR PRODUCING REFINED OILS FROM BOTANICAL PLANT MATTER USING A SUPERCRITICAL FLUID

TECHNICAL FIELD

The present invention relates to a process for producing refined oils from botanical plant matter in an efficient extraction process that uses high-pressure fluid.

BACKGROUND

Refined oils are used in many applications, such as pharmaceutical, cosmetic, and agricultural applications, resulting in a great demand to scale their production process effectively. There are three main ways to extract oils: cold pressing, expeller pressing, and solvent extraction. These current extraction processes, however, are not selective enough to produce refined oils. To refine them further, various steps are taken to improve the quality of the oil. One such step, known as winterization, is meant to remove plant waxes from the crude oil.

Current winterization methods used to produce refined oil from crude extracts are tedious, time consuming, labor intensive, and expensive. These conventional winterization processes involve dissolving a crude extract in a solvent such as an alcohol, and reducing the temperature of the mixture to precipitate the contaminating waxes and certain lipids. The waxes and lipids are separated from the solution and the solvent is boiled off to collect the winterized oil. If the waxes and lipids are not removed, the oil will have a lower concentration of the final product and will be murkier, making it less appealing. Waxes also could pose a health risk when they are included in oils used in vape cartridges, a common method of consuming *Cannabis* plant extracts.

Prior to this winterization process, the oils are generally extracted from the biomass using a solvent. The simplest solvent extraction examples are found in the extraction of organic compounds. For example, benzene, a non-polar solvent, is immiscible with water, a highly polar solvent. If there is a compound dissolved in the benzene which is also water soluble, mixing the benzene solution with water several times will remove the water-soluble compound. This is a common technique used in chemistry labs known as a "wash".

One application of solvent extraction is the chemical process commonly used to remove oil from vegetables, oilseeds, and different biomasses. For extracting vegetable oil, for example, hexane is the preferred solvent choice. Another solvent extraction application is found in the petrochemical refining industry. Extracted petroleum has numerous impurities and therefore must be purified before use. A special hydrocarbon solvent is mixed with the petroleum, and the impurities precipitate out of solution upon chilling the mixture. These impurities can then be easily separated, resulting in purified petroleum.

Each of these extraction methods use an organic or hydrocarbon solvent. The Food and Drug Administration (FDA) has been stringently imposing limits on the volume of organic solvents in ingestible products as many of these solvents pose major health risks. The use of high-pressure carbon dioxide ($CO_2$) as a solvent eliminates these legal limitations on solvent residues and the restrictions on use of conventional solvents in chemical processes. $CO_2$ is considered a suitable replacement for conventional solvents, such as hydrocarbons like hexane, ethanol etc., as it poses no risks to consumers. $CO_2$ can be brought to a supercritical state by being heated above 304 degrees Kelvin (304 K; 31° C.) and pressurized above 74 bar.

One $CO_2$ extraction application is the production of cannabinoid rich oils from the *Cannabis* plant. Running the extraction at high pressures and temperatures results in higher yield of the cannabinoids, but it could also result in higher extraction of undesirable waxes/oleoresins and other compounds, such as fats and chlorophyll. Thus, refining *Cannabis* extracts typically involves a winterization step. A polar solvent, usually ethanol, is added to the crude extract, heated to dissolve the crude oil, and then chilled to low temperatures, sometimes even below the freezing point. The waxes and lipids in the extract will precipitate over time, allowing them to be separated.

Another $CO_2$ extraction application is the production of refined oils from the hops plant. As with the production of cannabinoid rich oils from the *Cannabis* plant, running the extraction at high pressures and temperatures results in higher yield of the refined oil, and typically also results in higher extraction of undesirable waxes/oleoresins and other compounds. Thus, similar to refining oils from the *Cannabis* plant, refining hops extracts to produced refined oils also involves a winterization step wherein a polar solvent such as ethanol is added to the crude extract, heated to dissolve the crude oil, and then chilled to low temperatures to precipitate the waxes and lipids in the extract.

While these processes are successful, they are time-consuming and labor intensive, and use a significant amount of alcohol-based solvents. Moreover, the explosive potential of the solvents limits the scalability of the process. In short, the current process for producing refined oils is inefficient and cost prohibitive for large scale commercial applications. Alternatives for the winterization step are needed to make this process applicable for commercial usage.

The advantages of using supercritical fluid for extraction (SFE) and isolation of natural substances are well documented. See for example U.S. Pat. No. 5,252,729. Most current processes using supercritical technology will run the extraction process to generate a solution of higher yield that will also include waxes. As indicated above, a solvent winterization process is performed at low temperatures to remove these waxes. For example, U.S. Pat. No. 9,333,229 to Bjorncrantz presents a method for producing vape cartridges containing cannabinoids, especially CBD and THC, from crude *Cannabis* extract using a winterization step. The crude extract is dissolved in ethanol and chilled to below 273 K (0° C.) for at least an hour, followed by a cold filtration step to separate all waxy ballast and any substances that may smoke and burn upon cannabinoid vaporization. The ethanol is then distilled, and the refined oil is left behind. This refined oil/extract is then mixed with a solvent, namely propylene glycol, and other flavors and fragrances making it suitable to be vaped by consumers.

U.S. Pat. No. 8,895,078 to Mueller presents the use of $CO_2$ to extract the THC and CBD from plant material. A stream of extract in $CO_2$ passes through a diatomaceous earth filter to remove alkaloids, flavonoids, and chlorophylls, followed by passage into a separator where the primary extract is collected. The extract is dissolved in ethanol, frozen and filtered to remove undesirable waxes. Ethanol is evaporated under reduced pressure, and the remaining extract is heated at 353 K (80° C.) for two hours for decarboxylation to convert the acidic cannabinoids to their neutral forms.

While these prior art processes remove a portion of the waxes, improved processes are desirable that may be more efficient and may provide refined oils of higher quality.

SUMMARY

The presently disclosed invention overcomes many of the shortcomings of the prior art by providing an environmentally friendly and efficient process for the production of refined oils from botanical plant matter. The process generally includes the use of a high-pressure fluid extraction step and a novel separation step to remove unwanted contaminants from the extracted oil and thus provides a highly refined oil.

Accordingly, the present invention relates to a process for providing a refined oil from a biomass. The process generally comprises extracting a crude oil from the biomass in a first extraction vessel using a high-pressure solvent, such as supercritical carbon dioxide, followed by separation of contaminating waxes or lipids in one or more separating columns, wherein the crude extract is mixed with additional high-pressure solvent before delivery to the separating column(s). This additional solvent assists in dissolving the extracted oil and provides a refined oil having an improved final yield and higher purity.

Thus, according to certain aspects of the presently disclosed invention, the process comprises extracting a biomass using a high-pressure solvent to provide a first oil stream of extract dissolved in the solvent, mixing the first oil extract dissolved in the solvent with a medium-pressure solvent stream to provide a diluted oil extract, delivering the diluted oil extract to a medium-pressure separator column to separate contaminants from the diluted oil extract and provide a dilute refined oil, and delivering the dilute refined oil to a low-pressure separator column to evaporate the solvent and provide a refined oil product.

The present invention also relates to refined oil products produced using the inventive processes, wherein the refined oil products are substantially free of contaminants such as waxes, fatty acids, lipids, and oleoresins, and totally free of solvents other than the solvent used in the process.

According to certain aspects, the refined oil products produced using the inventive processes may be substantially free of all solvents, such as those used in the process. According to certain aspects, the solvent may be $CO_2$.

DETAILED DESCRIPTION OF THE DRAWING

Further advantages and features of the present invention result from the description of practical examples and from the drawings, wherein:

FIG. 1 is a schematic representation of a high-pressure process for extracting oils from botanical material according to certain aspects of the presently disclosed invention.

The illustrative embodiment in the drawing is not meant to be limiting; other embodiments may be utilized, and other changes may be made without departing from the spirit or scope of the subject matter presented herein.

DETAILED DESCRIPTION

In the following description, the present invention is set forth in the context of various alternative embodiments and implementations involving improved processes for the removal of undesirable waxes and lipids from oils refined from botanical plant matter. While the following description discloses numerous exemplary embodiments, the scope of the present patent application is not limited to the disclosed embodiments, but also encompasses combinations of the disclosed embodiments, as well as modifications to the disclosed embodiments.

Definitions

Various aspects of the novel processes and equipment used to provide those processes, and the refined oils produced by the disclosed processes, may be illustrated by describing components that are coupled, attached, and/or joined together, or process steps that are linked. As used herein, the terms "coupled", "attached", "linked", and/or "joined" are interchangeably used to indicate either a direct connection between two components or process steps or where appropriate, an indirect connection to one another through intervening or intermediate components or steps. In contrast, when a component is referred to as being "directly coupled", "directly attached", "directly linked", and/or "directly joined" to another component or process step, there are no intervening elements or steps shown in said examples.

Accordingly, in the processes described herein, the steps can be carried out in any order without departing from the principles of the invention, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

Various aspects of the novel processes and equipment used to provide those processes, and the refined oils produced by the disclosed processes may be described and illustrated with reference to one or more exemplary implementations. As used herein, the term "exemplary" means "serving as an example, instance, or illustration," and should not necessarily be construed as preferred or advantageous over other variations of the devices, systems, or processes disclosed herein. "Optional" or "optionally" means that the subsequently described event or circumstance may or may not occur, and that the description includes instances where the event occurs and instances where it does not. In addition, the word "comprising" as used herein means "including, but not limited to".

It must also be noted that as used herein and in the appended claims, the singular forms "a", "an", and "the" include the plural reference unless the context clearly dictates otherwise. For example, although reference is made to "an" oil, "a" wax, and "the" solvent, one or more of any of these components and/or any other components described herein can be used.

Moreover, other than in any operating examples, or where otherwise indicated, all numbers expressing, for example, quantities of ingredients used in the specification and claims are to be understood as being modified in all instances by the term "about". Accordingly, unless indicated to the contrary, the numerical parameters set forth in the following specification and appended claims are approximations that may vary depending upon the desired properties to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard variation found in their respective testing measurements.

Unless defined otherwise, all technical and scientific terms used herein have the same meanings as commonly understood by one of ordinary skill in the art.

"Substantially free", as used herein, is understood to mean inclusive of only trace amounts of a constituent. "Trace amounts" are those quantitative levels of a constituent that are barely detectable and provide no benefit to the functional properties of the subject composition, process or compositions formed therefrom. For example, a trace amount may constitute 1.0 wt. %, 0.5 wt. %, 0.1 wt. %, 0.05 wt. %, or even 0.01 wt. % of a component or constituent of any of the refined oils disclosed herein. "Totally free", as used herein, is understood to mean completely free of a component or constituent.

As used herein, "polar" refers to a molecule having a net dipole as a result of the opposing charges (i.e., having partial positive and partial negative charges) from polar bonds arranged asymmetrically. As used herein, "nonpolar" refers to a molecule having an equal sharing of electrons between the two atoms of a diatomic molecule or because of the symmetrical arrangement of polar bonds in a more complex molecule.

As used herein, "supercritical fluid extraction" or "SFE" refers to the process of separating one or more components (extractant) from another (matrix) using supercritical fluids as the extracting solvent. Extraction is usually from a solid matrix (e.g., botanical plant material), but can also be from liquids or resinous material (e.g., oils from the plant). Although numerous supercritical fluids can be used, carbon dioxide ($CO_2$) is preferred. Extraction conditions for supercritical fluids of the present invention are generally a multiple of the critical temperature of (e.g., 304 K for carbon dioxide) and critical pressure of (e.g., 74 bar for carbon dioxide) of the solvent. Addition of modifiers may alter these values slightly.

As used herein, the term "botanical starting material" may be taken to include the leaves, flowers, stems, bark, seeds, fruits, and roots of a wide range of plant materials. Exemplary plant materials include at least herbs, aromatics, and other medicinally relevant botanicals, such as *Cannabis*, hops, lavender, melaluca, green tea, etc. For example, a refined oil product of melaluca (tea tree oil) is an effective antifungal and antimicrobial agent, and has been found to have anti-inflammatory properties. Cinnamon oils derived from the bark, leaves, and roots of Cinnamon trees have been reported to contain compounds having anti-microbial and anti-inflammatory properties, and may be active against diabetes, cancer, heart disease, Alzheimer's and Parkinson's diseases, among others. *Cannabis* has long been used for fiber (hemp), for seed and seed oils, for medicinal purposes, and as a recreational drug. Cannabidiol oils, derived from *Cannabis*, have been connected to reducing the risk of certain cancers, as well as reducing pain, improving the conditions of the heart, and helping people get a good night's sleep. Hops have been grown in Europe since the 14th Century as a bitter substance for brewing beer, and were later discovered to contain lupulin, bitter resinous substances (lupulone, humulone) and essential oils in the strobiles from female plants. These lupulins are reputed to have drug like activities for relieving anxiety and inducing sleep.

As used herein, "*Cannabis*" refers to a genus of flowering plants that includes a single species, *Cannabis sativa*, which is sometimes divided into two additional species, *Cannabis indica* and *Cannabis ruderalis*. These three taxa are indigenous to Central Asia, and South Asia. In addition to the fiber (hemp), seed and seed oils, and dried leaves, various extracts including hashish and hash oil are also produced from the plant. The *Cannabis* can include any physical part of the plant material, including, e.g., the leaf, bud, flower, trichome, seed, or combination thereof. Likewise, the *Cannabis* can include any substance physically derived from *Cannabis* plant material, such as, e.g., kief and hashish.

Moreover, the term "*Cannabis*" may include subspecies, such as hemp, and plants that are the result of genetic crosses, self-crosses, or hybrids thereof.

The *Cannabis* plant material contains suitable and desirable compounds, useful in the refined oils described herein. The suitable and desirable compounds fall within one or more of the following classes of compounds: cannabinoids, terpenoids, and flavonoids. Preferably, the desirable compounds include cannabinoids.

As used herein, "cannabinoid" refers to a class of diverse chemical compounds that act on cannabinoid receptors on cells that repress neurotransmitter release in the brain. These receptor proteins include the endocannabinoids (produced naturally in the body by humans and animals), the phytocannabinoids (found in *Cannabis* and some other plants), and synthetic cannabinoids (manufactured chemically). The most notable cannabinoid is the phytocannabinoid $\Delta^9$-tetrahydrocannabinol (THC), the primary psychoactive compound of *Cannabis*. Cannabidiol (CBD) is another major constituent of the plant, representing up to 60% in extracts of the plant resin. There are at least 85 different cannabinoids isolated from *Cannabis*, exhibiting varied effects.

The refined oil produced using the methods and processes of the presently disclosed invention may be enriched with certain compounds relative to the botanical starting materials.

As used herein, "enrich" refers to an increase in the concentration or amount of one substance relative to the concentration or amount of another substance; or one material containing a higher concentration or amount of a substance compared to a second material's concentration or amount of that substance. The difference in the amount (weight/mass) can be at least about 1%, at least about 5%, at least about 10%, at least about 25%, at least about 50%, at least about 75%, or at least about 90%. Likewise, the difference in concentration can be at least about 1%, at least about 5%, at least about 10%, at least about 25%, at least about 50%, at least about 75%, or at least about 90%. In reference to "higher concentration" and "lower concentration," the difference in concentration can be at least about 1%, at least about 5%, at least about 10%, at least about 25%, at least about 50%, at least about 75%, or at least about 90%.

The refined oil produced using the methods and processes of the presently disclosed invention may have a lower concentration, relative to the botanical starting materials, of the undesired product (e.g., waxes, fatty acids, oleoresins, lipids).

As used herein, "relative concentration" refers to the concentration of a specified substance (or a combination of specified substances) that is present in a lower concentration ("lower relative concentration"), or is present in a higher concentration ("higher relative concentration"), as compared to the concentration of the same substances in the botanical starting materials. The increase (or decrease) can range anywhere from about 10% to 100,000 fold. In specific embodiments, the increase (or decrease) can be about 10% to 10,000 fold; about 20% to 1,000 fold; about 50% to 100 fold; about 2 fold to 100 fold; about 3 fold to 50 fold; or about 5 fold to 25 fold.

Aspects of the Invention

A goal of the presently disclosed invention is to provide a simple and efficient process for the production of a refined oil from a biomass, i.e., botanical starting material. To achieve this goal, the process generally comprises extracting a crude oil from a biomass in an extraction step that uses a high-pressure solvent such as supercritical carbon dioxide (i.e., process referred to as supercritical fluid extraction), followed by separation of contaminating waxes or lipids from the extracted oil in one or more separating steps that use the same solvent.

It has been found that supercritical fluid extraction (SFE) is the only extraction method capable of removing heavy metals and other toxins from the oils extracted from plant materials contaminated with heavy metals and toxins. Moreover, SFE with carbon dioxide is considered a green chemistry as the solvent has no negative impact on the environment. Thus, the refined oils provided by the extraction methods of the presently disclosed invention may be of a high purity having little to no contamination from heavy metals, toxins, waxes, lipids, and solvents, such as the standard hydrocarbon and/or alcohol solvents generally used in the prior art extraction methods.

Extraction of the oils from the botanical plant matter according to the presently disclosed invention is generally in an extraction vessel using a solvent maintained at a low temperature, such as at a temperature of about 0.75 to about 1.5 times the critical temperature of the solvent, and high pressure, such as about 0.5 to about 10 times the critical pressure of the solvent.

According to various aspects of the presently disclosed invention, the temperature in the extraction vessel may be about 0.75 to about 1.5 times the critical temperature of the solvent, such as about 0.8 to about 1.5, or about 0.9 to about 1.5, or about 1.0 to about 1.5, or about 1.1 to about 1.5, or about 1.2 to about 1.5, or about 0.75 to about 1.4, or about 0.75 to about 1.3, or about 0.75 to about 1.2, or about 0.75 to about 1.1, or about 0.75 to about 1.0, or about 0.8 to about 1.4, or about 0.8 to about 1.3, or about 0.8 to about 1.2, or about 0.8 to about 1.1, or about 0.9 to about 1.4, or about 0.9 to about 1.3, or about 0.9 to about 1.2, or about 0.9 to about 1.1, or about 1.0 to about 1.4, or about 1.0 to about 1.3 times the critical temperature of the solvent.

According to certain aspects of the presently disclosed invention, the pressure in the extraction vessel may be about 0.5 to about 10 times the critical pressure of the solvent, such as about 1 to about 10, or about 2 to about 10, or about 3 to about 10, or about 0.5 to about 9, or about 0.5 to about 8, or about 0.5 to about 7, or about 0.5 to about 6, or about 0.5 to about 5, or about 1 to about 9, or about 1 to about 8, or about 1 to about 7, or about 1 to about 6, or about 1 to about 5, or about 2 to about 8, or about 2 to about 7, or about 2 to about 6, or about 2 to about 5, or about 3 to about 6, or about 3 to about 5 times the critical pressure of the solvent.

The botanical plant matter or biomass may be provided as received from a grower, i.e., as first harvested (not dried), or as a dried material. Either may be comminuted or pulverized to provide an improved solid matrix having increased accessibility of the high-pressure solvent during extraction. Drying and comminution may be performed in either order. Additional steps of screening to remove undesirable materials (e.g., moldy raw materials frequently present in industrial supplies) may be included before comminution. The botanical plant material or biomass may be dried slowly, i.e., for at least an hour, at moderate temperatures, such as less than 333 K (60° C.). Typically, the water content of a dried plant material is not greater than 10%, such as between 4% and 10%. Comminution of the biomass may provide a powder material of less than 60 mesh, such as less than 40 mesh, or between 20 and 40 mesh.

This process extracts oils from the biomass, and may also extract small amounts of waxes, fatty acids, oleoresins, and certain lipids from the biomass. In order to remove these contaminants, the extracted oil is sent through at least a first separator column that is held at a low temperature, generally in the range of about 0.75 to about 1.25 times the critical temperature of the solvent, and a moderate pressure, such as about 0.5 to about 3 times the critical pressure of the solvent.

According to various aspects of the presently disclosed invention, the temperature in the first separator column may be about 0.75 to about 1.25 times the critical temperature of the solvent, such as about 0.8 to about 1.25, or about 0.85 to about 1.25, or about 0.9 to about 1.25, or about 0.95 to about 1.25, or about 0.75 to about 1.2, or about 0.75 to about 1.15, or about 0.75 to about 1.10, or about 0.75 to about 1.05, or about 0.75 to about 1.00, or about 0.8 to about 1.20, or about 0.8 to about 1.15, or about 0.8 to about 1.05, or about 0.85 to about 1.2, or about 0.85 to about 1.15, or about 0.85 to about 1.10, or about 0.8 to about 1.0 times the critical temperature of the solvent.

According to certain aspects of the presently disclosed invention, the pressure in the first separator column may be about 0.5 to about 3 times the critical pressure of the solvent, such as about 0.6 to about 3 times, or about 0.7 to about 3 times, or about 0.8 to about 3 times, or about 0.9 to about 3 times, or about 1 to about 3 times, or about 0.5 to about 2.5 times, or about 0.5 to about 2 times, or about 0.5 to about 1.5 times, or about 0.6 to about 2.5 times, or about 0.7 to about 2.0 times, or about 0.8 to about 1.5 times the critical pressure of the solvent.

During this first separation step, a small amount of the extracted oil may be precipitated. To rectify this situation, additional solvent (e.g., $CO_2$) is added to the stream before it enters the first separator. For example, the additional solvent may be added to the extracted material after it exits the extraction vessel at a temperature and pressure that is reduced as compared to those conditions in the extraction vessel. This additional solvent dissolves the precipitated oil such that little or no oil is collected in the first separator. The present inventors have found that this step is critical to increasing the efficiency of collecting the refined oil in a second separator.

The additional solvent may be added in an amount or a volume equal to about 5% v/v of a total volume of extracted oil plus solvent exiting the extraction vessel, such as in an amount equal to about 10% v/v, or about 20% v/v, or about 30% v/v, or about 50% v/v, or about 100% v/v, or even about 200% v/v added solvent:extracted oil plus solvent exiting the extraction vessel (i.e., 2:1 of [added solvent]:[extracted oil+solvent] exiting the extraction vessel, on a v/v basis).

The extracted oil purified in the first separator column may then be sent to a second separator column that is held at a temperature in the range of about 0.9 to about 1.25 times the critical temperature of the solvent, and a low pressure, such as about 0.4 to about 2 times the critical pressure of the solvent. In this second separator column, the solvent is evaporated to provide a refined oil product.

According to various aspects of the presently disclosed invention, the temperature in the second separator column may be about 0.9 to about 1.25 times the critical temperature of the solvent, such as about 0.95 to about 1.25, or about 1.0 to about 1.25, or about 0.9 to about 1.20, or about 0.9 to about 1.15, or about 0.9 to about 1.10, or about 0.9 to about 1.05, or about 0.9 to about 1.0 times the critical temperature of the solvent.

According to certain aspects of the presently disclosed invention, the pressure in the first separator column may be about 0.4 to about 2 times the critical pressure of the solvent, such as about 0.5 to about 2 times, or about 0.6 to about 2 times, or about 0.4 to about 1.8 times, or about 0.4 to about 1.6 times, or about 0.4 to about 1.4 times, or about 0.4 to about 1.2 times, or about 0.4 to about 1 times, or about 0.5 to about 1.5 times, or about 0.5 to about 1.2 times, or about 0.5 to about 1.0 times the critical pressure of the solvent.

Accordingly, the presently disclosed invention provides a modified in-line winterization process that increases the yield of refined oils and reduces or eliminates the need for alcohol-based solvents in post processing, thereby eliminating the time and labor of a conventional winterization process. All of these advantages enable this process to be safely used on a large commercial scale system.

The presently disclosed invention may be used to provide a refined oil from botanical starting materials, such as from the seeds, leaves, bark, fruit, flowers, stems, or roots of a wide range of plant materials (i.e., botanical starting material, or biomass).

An exemplary process according to various aspects of the presently disclosed invention is shown in FIG. 1. In a first step, a biomass may be loaded into an extraction vessel (4). Exemplary biomass includes botanical plant materials. According to certain aspects of the invention, the botanical plant materials are dried and comminuted.

A stream of solvent may be pumped into the extraction vessel (4) from a bulk solvent supply tank or an integral recirculation system. In a preferred embodiment, the solvent may be $CO_2$. Thus, as shown in FIG. 1, a $CO_2$ stream originating from a $CO_2$ supply (1) is split at a connecting tee (a) into two paths (A1 & A2) where a main stream of $CO_2$ flows into a first pump, i.e., "pump 1" (2). The system is pressurized by starting the first pump (2) and setting a flow rate to a desired level. A temperature for a preheater (3) may be set to the desired extraction temperature. Exemplary extraction temperatures include about 0.75 to about 1.5 times the critical temperature of the solvent. When the solvent is $CO_2$, which has a critical temperature of 304 K, the temperature of the $CO_2$ in the extraction vessel may be about 225 K to about 450 K. Exemplary extraction pressures include about 0.5 to about 10 times the critical pressure of the solvent. When the solvent is $CO_2$, which has a critical pressure of 74 bar, the pressure of the $CO_2$ in the extraction vessel may be about 37 bar to about 750 bar.

This stream of $CO_2$ flows through the extraction vessel (4) and extracts a product oil from the biomass. At this stage, the oil is not refined and may be contaminated with various waxes, fatty acids, oleoresins, and lipids. The extracted product (e.g., the desired oil plus the contaminants) may exit the extraction vessel along with the high-pressure solvent through an outlet travelling along path D to a first back pressure regulator (6) which may be set to the desired extraction pressure.

A second stream of $CO_2$ flows from the tee (a) along path A2 and into a second pump, i.e., "pump 2" (6). This stream of $CO_2$ may originate from the $CO_2$ supply (1), from a recycle system, such as a system that recycles the $CO_2$ from the end of the process (13), or from another source. A heat exchanger (7) cools this stream before it goes into the tee (f) where the two streams of $CO_2$ are combined, i.e., the second stream from path F2 and the stream exiting the extraction vessel F1.

The combined $CO_2$ stream (F) will flow through a medium pressure heat exchanger (8), which will chill the stream to the desired temperature. As mentioned above, exposing the stream (F1) to the reduced temperature and pressure conditions of the medium pressure heat exchanger (8) may cause a small amount of the extracted oil to precipitate. Mixing the extracted oil/solvent as it exits the extraction vessel (4) along path F1 with the additional solvent stream (F2) that is precooled before it enters the medium pressure heat exchanger (8) may prevent any precipitation of oil before entry to the first separator (9, medium pressure separator). As such, the cooled stream of $CO_2$ and unrefined oil will then flow along path G to a first separator (9).

The first separator will generally have a temperature of about 0.75 to about 1.25 times the critical temperature of the solvent. When the solvent is $CO_2$, which has a critical temperature of 304 K, the temperature of the $CO_2$ in the first separator may be about 225 K to about 380 K. Exemplary separator pressures include about 0.5 to about 3 times the critical pressure of the solvent. When the solvent is $CO_2$, which has a critical pressure of 74 bar, the pressure of the $CO_2$ in the separator may be about 35 bar to about 225 bar.

Nearly all the waxes and a very minimal amount of refined oil will precipitate in the medium pressure separator (9) and can be collected (P1). This fraction is shown as UD in FIG. 1 (i.e., Undesirable Fraction). The $CO_2$ with desired oil from the medium pressure separator outlet (H) will go through a second back pressure regulator (10) and a low-pressure heat exchanger (11), which will vaporize the $CO_2$. The vaporizing heat exchanger's (11) outlet stream (J) will then enter a low-pressure separator (12), where all the refined oil and a minimal amount of waxes will be collected (P2). This fraction is shown as RO in FIG. 1 (i.e., Refined Oil). The extract-free $CO_2$ will exit the low-pressure separator (12) along path K through a $CO_2$ outlet (13) where it can be vented or recycled.

The second separator will generally have a temperature of about 0.9 to about 1.25 times the critical temperature of the solvent, and a pressure about 0.4 to about 2 times the critical pressure of the solvent. When the solvent is $CO_2$, which has a critical temperature of 304 K and a critical pressure of 74 bar, the temperature of the $CO_2$ in the second separator may be about 274 K to about 380 K and the pressure of the $CO_2$ may be about 30 bar to about 150 bar.

Thus, as detailed herein, the present invention relates to a process for providing a refined oil from a biomass. The process generally comprises extracting a crude oil from a biomass in a first extraction vessel using a high-pressure solvent, such as supercritical carbon dioxide, followed by separation of contaminating waxes or lipids in one or more separating columns.

According to certain aspects, the extraction uses a high-pressure solvent stream to provide a first oil extract dissolved in the solvent. The first oil extract dissolved in the solvent is mixed with a medium-pressure solvent stream to provide a diluted oil extract. This diluted oil extract is delivered to a medium-pressure separator column to separate contaminants from the diluted oil extract and provide a dilute refined oil, which is then delivered to a low-pressure separator column to evaporate the solvent and provide a refined oil product.

As indicated above, the refined oil produced by the method disclosed in FIG. 1 is substantially free of waxes, oleoresins, or certain lipids, and may also be substantially or totally free of solvents, such as the solvent used in the extraction process (e.g., $CO_2$).

In an exemplary embodiment, the refined oil may be enriched for, or have a high concentration of, cannabinoids such as tetra-hydrocannabinol (THC) and cannabidiol (CBD).

According to certain aspects, the process can be used to obtain refined oils having high concentrations of cannabinoids such as tetra-hydrocannabinol (THC) and cannabidiol (CBD). According to certain aspects, the botanical starting material may be *Cannabis*, or a plant material comprising cannabinoids.

As example, and according to certain aspects, the presently disclosed invention may be used to provide a refined oil product from a *Cannabis* plant, i.e., *Cannabis* concentrate. The refined oil can include a higher relative concentration of cannabinoids, or a lower relative concentration of contaminants such as waxes, oleoresins, or certain lipids, relative to the starting *Cannabis* plant materials. As such, the concentration of cannabinoids will be higher in the *Cannabis* concentrate compared to the concentration of cannabinoids in the *Cannabis* plant material. Likewise, the concentration of contaminants will be lower in the *Cannabis* concentrate compared to their concentration in the *Cannabis* plant material.

According to certain aspects, the desired extract of *Cannabis* (i.e., extract produced using a process of the presently disclosed invention), relative to the undesired extract of *Cannabis* (i.e., extract produced using a prior art process), will include a lower concentration of the undesired product. According to certain aspects, the undesired extract of *Cannabis*, relative to the desired extract of *Cannabis*, will include a lower concentration of the desired product (e.g., cannabinoids).

As such, the presently disclosed process can be employed to selectively obtain one or more desired substances from a botanical starting material, such as the *Cannabis* plant material, while selectively excluding one or more undesired substances. For example, the presently disclosed invention may provide a refined oil of *Cannabis*, relative to the starting plant material, enriched with the desired product (e.g., cannabinoids). According to certain aspects, the desired extract of *Cannabis* (i.e., extract produced using a process of the presently disclosed invention), relative to the undesired extract of *Cannabis* (e.g., extracts using prior art processes), will be enriched with the desired product (e.g., cannabinoids). According to certain aspects, the undesired extract of *Cannabis*, relative to the desired extract of *Cannabis*, will be enriched with the undesired product (e.g., waxes, fatty acids, oleoresins, lipids).

EXAMPLES

With reference to FIG. 1, exemplary operating conditions for production of refined oils from a biomass according to the presently disclosed invention are listed in Tables 1-3. In each example, the undesirable fraction (collected mass at P1; listed as UD in each table) made up less than 5% of the refined oil (collected mass at P2; listed as RO in each table).

Tables 1 and 2 show process results for refining oil from *Cannabis* plant material, and Table 3 shows process results for refining oil from hops plant material. The data in Tables 1 and 2 show the process to be linearly scalable within the range of starting materials tested, i.e., about 10% of the starting material is recovered as a refined oil (RO), and less than 5% is lost as an undesirable fraction (UD). Moreover, the data in Table 3 shows that the process is perfected to work on a wide variety of starting botanical materials. In fact, the inventive process disclosed herein provided a greater amount of refined oil from the hops material (i.e., greater than 20% of the starting material is recovered as a refined oil), while the amount of undesirable fraction romved remained essentially the same (i.e., less than 5% is lost as an undesirable fraction (UD).

TABLE 1

| Flow path | Line # | Pressure (bar-g) | Temperature (K) | Solvent Flowrate (kg/min) | Collection Mass (g) | Fraction Collected | Biomass (kg) |
|---|---|---|---|---|---|---|---|
| 2 > 3 > 4 | C | 300 | 303 | 0.75 | — | — | 1.6 |
| 2 > 3 > 4 > 5 | D | 300 | 303 | 0.75 | — | — | — |
|  | F1 | 120 | 293 | 0.75 | — | — | — |
| 6 > 7 | F2 | 80 | 283 | 0.75 | — | — | — |
| 8 | F | 80 | 288 | 1.75 | — | — | — |
|  | G | 80 | 283 | 1.75 | — | — | — |
| 9 | H | 80 | 283 | 1.75 | — | — | — |
|  | P1 |  |  |  | 8 | UD | — |
| 10 | I | 60 | 271 | 1.75 | — | — | — |
| 11 | J | 60 | 298 | 1.75 | — | — | — |
| 12 | K | 60 | 298 | 1.75 | — | — | — |
|  | P2 |  |  |  | 157 | RO | — |

TABLE 2

| Flow path | Line # | Pressure (bar-g) | Temperature (K) | Solvent Flowrate (kg/min) | Collection Mass (g) | Fraction Collected | Biomass (kg) |
|---|---|---|---|---|---|---|---|
| 2 > 3 > 4 | C | 300 | 303 | 1 | — | — | 3.4 |
| 2 > 3 > 4 > 5 | D | 300 | 303 | 1 | — | — | — |
|  | F1 | 80 | 293 | 1 | — | — | — |
| 6 > 7 | F2 | 80 | 283 | 1 | — | — | — |
| 8 | F |  |  |  |  | — |  |
|  | (F1 + F2) | 80 | 288 | 1.85 | — |  | — |
|  | G | 80 | 283 | 1.85 | — | — | — |
| 9 | H | 80 | 283 | 1.85 | — | — | — |
|  | P1 |  |  |  | 15 | UD | — |
| 10 | I | 55 | 271 | 1.85 | — | — | — |
| 11 | J | 55 | 298 | 1.85 | — | — | — |
| 12 | K | 55 | 298 | 1.85 | — | — | — |
|  | P2 |  |  |  | 330 | RO | — |

TABLE 3

| Flow path | Line # | Pressure (bar-g) | Temperature (K) | Solvent Flowrate (kg/min) | Collection Mass (g) | Fraction Collected | Biomass (kg) |
|---|---|---|---|---|---|---|---|
| 2 > 3 > 4 | C | 300 | 308 | 0.5 | — | — | 1.06 |
| 2 > 3 > 4 > 5 | D | 300 | 308 | 0.5 | — | — | — |
|  | F1 | 80 | 298 |  | — | — | — |
| 6 > 7 | F2 | 80 | 283 | 0.5 | — | — | — |
| 8 | F | 80 | 291 | 1 | — | — | — |
|  | G | 80 | 289 |  | — | — | — |
| 9 | H | 80 | 289 | 1 | — | — | — |
|  | P1 |  |  |  | 12.3 | UD | — |
| 10 | I | 60 | 271 | 1 | — | — | — |
| 11 | J | 60 | 308 | 1 | — | — | — |
| 12 | K | 60 | 308 | 1 | — | — | — |
|  | P2 |  |  |  | 242 | RO | — |

The following aspects are disclosed in this application:

Aspect 1: A process for producing a refined oil product from a biomass, the process comprising: extracting a biomass using a high-pressure solvent stream to provide a first oil extract dissolved in the solvent, mixing the first oil extract dissolved in the solvent with a medium-pressure solvent stream to provide a diluted oil extract, delivering the diluted oil extract to a medium-pressure separator column to separate contaminants from the diluted oil extract and provide a dilute refined oil.

Aspect 2: The process according to aspect 1, further comprising, delivering the dilute refined oil to a low-pressure separator column to evaporate the solvent and provide a refined oil product.

Aspect 3: The process according to aspects 1 or 2, wherein the biomass comprises a botanical plant material.

Aspect 4: The process according to any one of aspects 1 to 3, wherein the biomass comprises a botanical plant material having cannabidiols, such as a *Cannabis* plant material, and the refined oil product is enriched for cannabidiols.

Aspect 5: The process according to any one of aspects 1 to 4, wherein the contaminants comprise waxes, lipids, oleoresins, fatty acids, and combinations thereof.

Aspect 6: The process according to any one of aspects 1 to 5, wherein extracting the biomass is at an extraction pressure of 0.5 to 10 times the critical pressure of the solvent and an extraction temperature of 0.75 to 1.5 times the critical temperature of the solvent.

Aspect 7: The process according to any one of aspects 1 to 6, wherein the medium-pressure solvent stream is provided at a pressure of 0.5 to 3 times the critical pressure of the solvent and a temperature of 0.75 to 1.25 times the critical temperature of the solvent.

Aspect 8: The process according to any one of aspects 1 to 7, wherein the medium-pressure solvent stream is provided in a volume of at least 5% v/v to a total volume of the first oil extract (i.e., the first oil extract dissolved in the solvent).

Aspect 9: The process according to any one of aspects 1 to 8, wherein the high-pressure solvent stream is provided at about the critical temperature and at least two-times the critical pressure.

Aspect 10: The process according to any one of aspects 1 to 9, wherein the medium-pressure solvent stream is provided at subcritical temperature and about critical pressure.

Aspect 11: The process according to any one of aspects 1 to 10, wherein the diluted oil extract is maintained on the medium-pressure separator column at a pressure of 0.5 to 3 times the critical pressure of the solvent and a temperature of 0.75 to 1.25 times the critical temperature of the solvent.

Aspect 12: The process according to any one of aspects 2 to 11, wherein the dilute refined oil is maintained on the low-pressure separator column at a pressure of 0.4 to 2 times the critical pressure of the solvent and a temperature of 0.9 to 1.25 times the critical temperature of the solvent.

Aspect 13: The process according to any one of aspects 2 to 12, wherein the low-pressure separator column is maintained at subcritical pressure to evaporate the solvent, or wherein the low-pressure separator column is maintained at subcritical pressure and temperature to evaporate the solvent.

Aspect 14: The process according to any one of aspects 1 to 13, wherein the process uses only a single solvent.

Aspect 15: The process according to any one of aspects 14, wherein the single solvent is carbon dioxide ($CO_2$).

Aspect 16: The process according to aspect 15, wherein the extraction is at an extraction temperature of about 225 K to about 450 K and an extraction pressure of about 37 to about 750 bar, or an extraction temperature of about 225 K to about 450 K and an extraction pressure of about 200 to about 500 bar.

Aspect 17: The process according to aspect 15, wherein the medium-pressure solvent stream is provided at a temperature of about 225 K to about 380 K and a pressure of about 35 to about 225 bar.

Aspect 18: The process according to aspect 15, wherein medium-pressure separator column is maintained at a separation pressure of about 35 to 225 bar and a separation temperature of about 225 to about 380.

Aspect 19: The process according to aspect 15, wherein low-pressure separator column is maintained at a separation pressure of about 30 to 150 bar and a separation temperature of about 279 to about 380.

Aspect 20: A refined oil product made by the process according to any one of aspects 1 to 19, wherein the refined oil product is substantially free of waxes, lipids, oleoresins, fatty acids, and combinations thereof, and totally free of hydrocarbon and/or alcohol solvents.

Aspect 21: A refined oil product made by the process according to any one of aspects 1 to 19, wherein the refined oil product is substantially free of waxes, lipids, oleoresins, fatty acids, and combinations thereof, and totally free of hydrocarbon and/or alcohol solvents, and wherein the refined oil product is enriched for CBD.

Aspect 22: A process for producing a refined oil product from a *Cannabis* plant material, the process comprising: extracting the *Cannabis* plant material using a high-pressure $CO_2$ stream to provide a first oil extract dissolved in $CO_2$, wherein the extraction is at an extraction temperature of 225 K to 450 K and an extraction pressure of 37 bar to 750 bar; mixing the first oil extract dissolved in $CO_2$ with a medium-pressure $CO_2$ stream to provide a diluted oil extract, wherein the medium-pressure $CO_2$ stream is provided at a temperature of 225 K to 380 K and a pressure of 35 bar to 225 bar in a volume of at least 10% v/v to a total volume of the first oil extract dissolved in $CO_2$; delivering the diluted oil extract to a medium-pressure separator column to separate contaminants from the diluted oil extract and provide a dilute refined oil; and delivering the dilute refined oil to a low-pressure separator column to evaporate the $CO_2$ and provide a refined oil product, wherein the refined oil product is enriched for cannabidiols, and substantially free of waxes, lipids, oleoresins, fatty acids, and combinations thereof.

While the presently disclosed invention has been described in detail, it should be appreciated by those skilled in the art that various modifications and alternations and applications could be developed in light of the overall teachings of the disclosure. Accordingly, the particular systems, compositions, and processes disclosed are meant to be illustrative only and not limiting as to the scope of the invention.

What is claimed is:

1. A process for producing a refined oil product from a biomass, the process comprising:
   extracting a biomass using a high-pressure solvent stream to provide a first oil extract dissolved in solvent;
   mixing the first oil extract dissolved in solvent with a medium-pressure solvent stream to provide a diluted oil extract; and
   delivering the diluted oil extract to a medium-pressure separator column to separate contaminants from the diluted oil extract and provide a dilute refined oil.

2. The process according to claim 1, further comprising:
   delivering the dilute refined oil to a low-pressure separator column to evaporate the solvent and provide a refined oil product.

3. The process of claim 1, wherein the solvent is carbon dioxide ($CO_2$).

4. The process of claim 1, wherein the biomass comprises a botanical plant material.

5. The process of claim 4, wherein the botanical plant material comprises *Cannabis*, and the refined oil product is enriched for cannabidiols.

6. The process of claim 1, wherein the process removes at least 95% of the contaminants from the diluted oil extract, wherein the contaminants comprise waxes, lipids, oleoresins, fatty acids, and combinations thereof.

7. The process of claim 1, wherein extracting the biomass is at an extraction pressure is 0.5 to 10 times the critical pressure of the solvent, and the extraction temperature is 0.75 to 1.5 times the critical temperature of the solvent.

8. The process of claim 1, wherein the medium-pressure solvent stream is provided at a pressure of 0.5 to 3 times the critical pressure of the solvent, and a temperature of 0.75 to 1.25 times the critical temperature of the solvent.

9. The process of claim 1, wherein the medium-pressure solvent stream is provided in a volume of at least 5% v/v to a total volume of the first oil extract dissolved in the solvent.

10. The process of claim 1, wherein the medium-pressure solvent stream is provided at subcritical temperature and about critical pressure.

11. The process of claim 1, wherein the diluted oil extract is maintained on the medium-pressure separator column at a pressure of 0.5 to 3 times the critical pressure of the solvent and a temperature of 0.75 to 1.25 times the critical temperature of the solvent.

12. The process of claim 2, wherein the dilute refined oil is maintained on the low-pressure separator column at a pressure of 0.4 to 2 times the critical pressure of the solvent and a temperature of 0.9 to 1.25 times the critical temperature of the solvent.

13. The process of claim 2, wherein the low-pressure separator column is maintained at subcritical pressure and subcritical temperature to evaporate the solvent.

14. A process for producing a refined oil product from a biomass, the process comprising:
   extracting a biomass using a $CO_2$ stream to provide a first oil extract dissolved in $CO_2$, wherein the extracting is at an extraction temperature of 225 K to 450 K and an extraction pressure of 37 bar to 750 bar;
   mixing the first oil extract dissolved in $CO_2$ with a medium pressure $CO_2$ stream to provide a diluted oil extract, wherein the medium pressure $CO_2$ stream is provided at a temperature of 225 K to 380 K and a pressure of pressure of 35 bar to 225 bar; and
   delivering the diluted oil extract to a medium pressure separator column to separate contaminants from the diluted oil extract and provide a dilute refined oil, wherein the medium pressure separator column is maintained at a separation temperature of 225 K to 380 K and a separation pressure of 35 to 225 bar,
   wherein the process uses only $CO_2$ as solvent and does not include any other solvents.

15. The process of claim 14, further comprising:
delivering the dilute refined oil to a low pressure separator column to evaporate the $CO_2$ and provide a refined oil product, wherein the low pressure separator column is maintained at a temperature 279K to 380K and a pressure of 30 bar to 150 bar.

16. The process of claim 14, wherein the biomass comprises a botanical plant material.

17. The process of claim 14, wherein the botanical plant material comprises *Cannabis*, and the refined oil product is enriched for cannabidiols.

18. A process for producing a refined oil product from a *Cannabis* plant material, the process comprising:
extracting the *Cannabis* plant material using a high-pressure $CO_2$ stream to provide a first oil extract dissolved in $CO_2$, wherein the extraction is at an extraction temperature of 225 K to 450 K and an extraction pressure of 37 bar to 750 bar;
mixing the first oil extract dissolved in $CO_2$ with a medium-pressure $CO_2$ stream to provide a diluted oil extract, wherein the medium-pressure $CO_2$ stream is provided at a temperature of 225 K to 380 K and a pressure of 35 bar to 225 bar in a volume of at least 10% v/v to a total volume of the first oil extract dissolved in $CO_2$;
delivering the diluted oil extract to a medium-pressure separator column to separate contaminants from the diluted oil extract and provide a dilute refined oil; and
delivering the dilute refined oil to a low-pressure separator column to evaporate the $CO_2$ and provide a refined oil product,
wherein the refined oil product is enriched for cannabidiols, and substantially free of waxes, lipids, oleoresins, fatty acids, and combinations thereof.

* * * * *